United States Patent

Breuer et al.

[11] 4,171,435
[45] Oct. 16, 1979

[54] [(THIOALKYL)THIOACETYL]CEPHALOSPORIN DERIVATIVES

[75] Inventors: Hermann Breuer; Uwe D. Treuner, both of Regensburg, Fed. Rep. of Germany

[73] Assignee: E. R. Squibb & Sons, Inc., Princeton, N.J.

[21] Appl. No.: 495,598

[22] Filed: Aug. 8, 1974

[51] Int. Cl.² .................. C07D 501/28; C07D 501/32; C07D 501/34; A61K 31/545

[52] U.S. Cl. ....................................... 544/29; 544/28; 424/246

[58] Field of Search ................ 260/243 C; 544/28, 29

[56] References Cited

FOREIGN PATENT DOCUMENTS 948076 1/1964 United Kingdom ................ 260/243 C

OTHER PUBLICATIONS

Lewis et al., Antimicrobial Agents and Chemeotherapy, (1968), pp. 109–114, (1969).

*Primary Examiner*—Donald G. Daus
*Assistant Examiner*—Diana G. Rivers
*Attorney, Agent, or Firm*—Lawrence S. Levinson; Merle J. Smith; Stephen B. Davis

[57] ABSTRACT

[(Thioalkyl)thioacetyl]cephalosporin derivatives of the formula

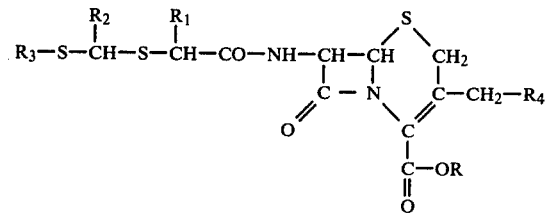

wherein R is hydrogen, lower alkyl, phenyl-lower alkyl, tri(lower alkyl)silyl, a salt forming ion, or the group

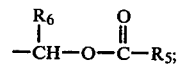

$R_1$ is hydrogen, lower alkyl, phenyl, thienyl or furyl; $R_2$ and $R_6$ each is hydrogen or lower alkyl; $R_3$ and $R_5$ each is lower alkyl, phenyl or phenyl-lower alkyl and $R_4$ is hydrogen, hydroxy or lower alkanoyloxy; are useful as antimicrobial agents.

15 Claims, No Drawings

[(THIOALKYL)THIOACETYL)]CEPHALOSPORIN DERIVATIVES

Summary of the Invention

This invention relates to new [(thioalkyl)thioacetyl]-cephalosporin derivatives of the formula

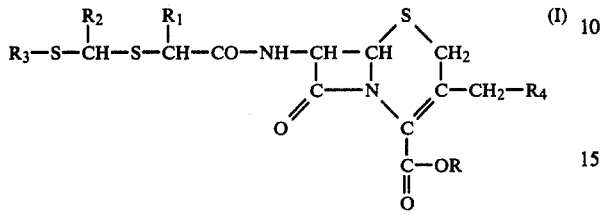

R represents hydrogen, lower alkyl, phenyl-lower alkyl, tri (lower alkyl)silyl, a salt forming ion or the group

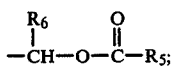

$R_1$ represents hydrogen, lower alkyl, phenyl, thienyl or furyl; $R_2$ and $R_6$ each represents hydrogen or lower alkyl; $R_3$ and $R_5$ each represents lower alkyl, phenyl or phenyl-lower alkyl; and $R_4$ represents hydrogen, hydroxy or lower alkanoyloxy.

The preferred members within each group are as follows: R is hydrogen, alkali metal, diphenylmethyl or

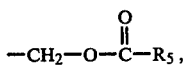

especially hydrogen, pivaloyoxy, sodium or potassium; $R_1$ is hydrogen or phenyl; $R_2$ is hydroen; $R_3$ is lower alkyl, phenyl or phenyl-lower alkyl, especially benzyl; $R_4$ is hydrogen or acetoxy; and $R_5$ is methyl or t-butyl.

Detailed Description of the Invention

The various groups represented by the symbols have the meanings defined below and these definitions are retained throughout this specification.

The lower alkyl groups are the straight and branched chain hydrocarbon groups in the series from methyl to heptyl, methyl and ethyl being generally preferred.

The lower alkanoyloxy groups represented by $R_4$ include the acyl radicals of lower fatty acids containing alkyl radicals of the type described above, e.g., acetoxy, propionoxy, butyryloxy, etc., acetoxy being preferred.

The phenyl-lower alkyl radicals include a phenyl ring attached to a lower alkyl group of the kind described above as well as those containing two phenyl groups such as benzhydryl.

The salt forming ions represented by R are metal ions, e.g., alkali metal ions such as sodium or potassium, alkaline earth metal ions such as calcium or magnesium or an amine salt ion, e.g., a (lower alkyl)amine like methylamine or triethylamine, or a cycloalkylamine like dicyclohexylamine, etc.

The new [(thioalkyl)thioacetyl]cephalosporin derivatives of this invention are produced by reacting a 7-aminocephalosporanic acid compound [which includes 7-aminocephalosporanic acid (7-ACA), 7-amino-3-desacetoxycephalosporanic acid (7-ADCA) and other derivatives] of the formula

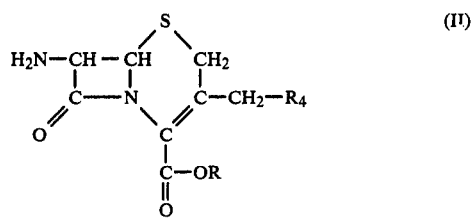

or derivative thereof with a [(thioalkyl)thio]acetic acid of the formula

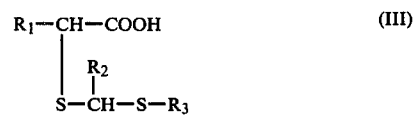

or an acid halide or anhydride thereof.

The derivatives of II referred to include, for example, the triethylamine derivative, benzhydryl ester or the like. The acid halide of III is preferably the chloride. The reaction may also be carried out in the presence of dicyclohexylcarbodiimide or the like.

A preferred method is the reaction between the 7-aminocephalosporanic acid compound and the [(thioalkyl)-thio]acetic acid which is effected, for example, by dissolving or suspending the latter or its acid chloride or anhydride in an inert organic solvent such as chloroform, tetrahydrofuran, methylene chloride, dioxane, benzene or the like, and adding, at a reduced temperature of about 0 to $-20°$ C about an equimolar amount of the 7-ACA or 7-ADCA compound, preferably the diphenylmethyl ester, in the presence of an activating compound such as dicyclohexylcarbodiimide. The product of the reaction is then isolated by conventional procedures, e.g., by concentration or evaporation of the solvent. The diphenylmethyl ester is converted to the free acid, e.g., with trifluoroacetic acid and anisole. Any of the salts can then be produced by conventional treatment, e.g., with potassium ethyl hexanoate, sodium bicarbonate or the like.

Another preferred method involves the reaction of a 7-aminocephalosporanic acid with the acid halide of the acid of formula III in aqueous alkaline medium.

When R is the acyloxymethyl group

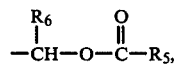

this group may be introduced into the 7-aminocephalosporanic acid moiety prior to the reaction with the [(thioalkyl)-thio]acetic acid or derivative by treatment with one to two moles of a halomethyl ester of the formula

wherein hal is halogen, preferably chlorine or bromine, in an inert organic solvent such as dimethylformamide, acetone, dioxane, benzene or the like, at about ambient temperature or below.

The [(thioalkyl)thio]acetic acid of formula III is produced by reacting a mercaptoacetic acid of the formula

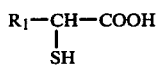 (V)

with a halogenated compound of the formula

 (VI)

in the presence of a base like triethylamine in a solvent like tetrahydrofuran and hydrolyzing the ester formed in the process.

Alteratively, when the acid halide is used to react with the 7-aminocephalosporanic acid compound, a mercaptan $R_3$—SMe (wherein Me is a metal like potassium) is made to react with a haloester of the formula

 (VII)

to obtain the intermediate of the formula

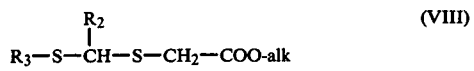 (VIII)

Treatment with a base, e.g., an alkali metal hydroxide, converts the ester to a salt which is then converted to the acid chloride with a halogenation agent like oxalyl chloride.

Further process details are also provided in the illustrative examples.

Certain of the compounds of this invention may exist in different optically active forms. The various stereoisomeric forms as well as the racemic mixtures are within the scope of the invention.

the compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They can be used as antibacterial agents in a prophylactic manner, e.g., in cleaning or disinfecting compositions, or otherwise to combat infections due to organisms such as those named above, and in general may be utilized in a manner similar to cephradine and other cephalosporins. For example, a compound of formula I or a physiologically acceptable salt thereof can be used in various animal species in an amount of about 1 to 150 mg./kg., daily, orally or parenterally, in single or two to four divided doses to treat infections of bacterial origin, e.g., 5.0 mg./kg. in mice.

Up to about 600 mg. of a compound of formula I or a physiologically acceptable salt thereof is incorporated in an oral dosage form such as tablet capsule or exilir or in an injectable form in a sterile aqueous vehicle prepared according to conventional pharmaceutical practice.

They can also be used in cleaning or disinfecting compositions at a concentration of about 0.01 to 1% by weight of such compounds admixed with, suspended or dissolved in conventional inert dry or aqueous carriers for application by washing or spraying.

The following examples are illustrative of the invention. All temperatures are in degrees celsius. Additional variations are produced in the same manner by appropriate substitution in the starting material.

EXAMPLE 1

[(Methylthio)methyl]thioactic acid, triethylamine salt 30.4 ml. (0.22 mol.) of triethylamine are added to 9.21 gms. (0.1 mol.) of mercaptoacetic acid in 100 ml. of absolute tetrahydrofuran. 9.65 gms. of (methylthio)methyl chloride dissolved in 10 ml. of tetrahydrofuran are added dropwise at 0°. The mixture is stirred at room temperature for two days. The mixture is filtered and the filtrate is concentrated under vacuum. The residue [(methylthio)methyl]thioacetic acid, triethylamine salt is used further without purification.

EXAMPLE 2

[(Methylthio)methyl]thioacetyl chloride

The product of Example 1 is dissolved in 125 ml. of methylene chloride and a solution of 25.4 gms. of oxalyl chloride in 50 ml. of methylene chloride is added dropwise at 110°. This is stirred for one hour at room temperature and then concentrated. Ether is added to the residue and the mixture is filtered. The filtrate is concentrated and the residue is distilled under vacuum to obtain 6.6 gms. of [(methylthio)methyl]thioacetyl chloride, b.p.$_{0.01}$ 71°–74°.

EXAMPLE 3

3-[(Acetyloxy)methyl]-7-[[[[(methylthio)methyl]thio]acetyl]amino]-8-oxo-5-thia-1-azabicyclo[4.2.0]oct-2-ene-2-carboxylic acid 5.44 gms. of 7-aminocephalosporanic acid are brought into solution in a mixture of 35 ml. of water and 35 ml. of acetone at 0–5° by the addition of saturated sodium bicarbonate solution. A solution of 4.42 gms. of [(methylthio)methyl]thioacetyl chloride in 10 ml. of acetone are added dropwise at a pH of about 7.5. The pH is held at 7.5 by the addition of sodium bicarbonate. After 30 minutes, 100 ml. of ethyl acetate are added and the pH is brought to 1.5 with 2N hydrochloric acid. The ethyl acetate solution is concentrated, extracted with methylene chloride, filtered, concentrated and the product, 3-[(acetyloxy)methyl]-7-[[[[(methylthio)methyl]thio]acetyl]amino]-8-oxo-5-thia-1-azabicyclo[4.2.0]oct-2-ene-2-carboxylic acid, is precipitated from the residue with ethyl acetate/petroleum ether, m.p. 118°–120° (dec.).

EXAMPLE 4

3-[(Acetyloxy)methyl]-7-[[[[(methylthio)methyl]thio]acetyl]amino]-8-oxo-5-thia-1-azabicyclo[4.2.0]oct-2-ene-2-carboxylic acid, potassium salt 1.5 gms. of 3-[(acetyloxy)methyl]-7-[[[[(methylthio)methyl]thio]acetyl]amino]-8-oxo-5-thia-1-azabicyclo[4.2.0]oct-2-ene-2-carboxylic acid dissolved in 5 ml. of methanol are added to a 2 N solution of potassium ethyl hexanoate in n-butanol to obtain 1.3 gms. of crystalline 3-[(acetyloxy)methyl]-7-[[[[(methylthio)methyl]thio]acetyl]amino-8-oxo-5-thia-1-azabicyclo[4.2.0]oct-2-ene-2-carboxylic acid, potassium salt, m.p. 120°–122° (dec.).

EXAMPLE 5

DL-α-[[(Methylthio)methyl]thio]benzeneacetic acid, (methylthio) methyl ester 16.8 gms. of α-phenylmercaptoacetic acid and 28.9 gms. of (methylthio)methyl chloride are dissolved in 100 ml. of absolute tetrahydrofuran and 41.4 ml. of triethylamine are added dropwise at 0°. The mixture is stirred overnight at room temperature, filtered, concentrated and the residue is distilled under vacuum to obtain 12.9 gms. of DL-60-[[(methylthio)methyl]thio]benzeneacetic acid, (methylthio) methyl ester, b.p.$_{0.05}$ 178°–180°.

EXAMPLE 6

DL-α-[[(Methylthio)methyl]thio]benzeneacetic acid 2.9 gms. of DL-α-[[(methylthio)methyl]thio]benzene acetic acid, (methylthio)methyl ester are dissolved in 10 ml. of ethanol. 20 ml. of 1 N alcoholic sodium hydroxide solution are added and the mixture is permitted to stand overnight. This is then concentrated, the residue is dissolved in water, the aqueous solution is extracted once with ether, then acidified and the oil is extracted with ether. After drying with magnesium sulfate and evaporating the solvent 1.8 gms. of DL-α-[[(methylthio)methyl]thio]benzeneacetic acid are obtained as an oil.

EXAMPLE 7

DL-3-[(Acetyloxy)methyl]-7β-[[[[(methylthio)methyl]thio]phenylacetyl]amino]-8-oxo-5-thia-1-azabicyclo[4.2.0]oct-2-ene-2-carboxylic acid, diphenylmethyl ester A solution of 4.54 gms. (0.022 mol.) of dicycohexylcarbodiimide in 40 ml. of absolute terahydrofuran is added at 0° to a solution of 8.76 gms. (0.02 mol.) of 7-aminocephalosporanic acid, diphenylmethyl ester and 5.47 gms. (0.024 mol.) of DL-α-[[(methylthio)methyl]thio]benzeneacetic acid in 100 ml. of absolute terahydrofuran. This is stirred for 90 minutes at 0° and 90 minutes at room temperature, then filtered and the filtrate is concentrated. The residue (9.8 gms.) is purified on a column of 500 gms of Kieselgel (Merck). The column is eluted with toluene/dioxane (80:20) and fractions of about 40 ml. each are collected. The product, DL-3-[(acetyloxy)mthyl]-7β-[[[[(methylthio)methyl]thio]phenylacetyl]amino]-8-oxo-5-thia-1-azabicyclo[4.2.0]oct-2-ene-2-carboxylic acid, diphenylmethyl ester, is obtained from fractions 13, 14 and 15 in chromatographically pure form.

EXAMPLE

DL-3-[(Acetyloxy)methyl]-7β-[[[[(methylthio)methyl]thio]phenylacetyl]amino]-8-oxo-5-thia-1-azabicyclo[4.2.0]oct-2-ene-2-carboxylic acid 1.9 gms. of the product of Example 7 are dissolved in 14 ml. of anisole and 39 ml. of trifluoroacetic acid are added while cooling with ice. This is then concentrated after 10 minutes. The residue is purified by dissolving in 10 ml. of methanol and treating with a 10% solution of dicyclohexylamine in isopropanol. 1.4 gms. of the dicyclohexylamine salt of DL-3-[(acetyloxy)methyl]-7β-[[[[(methylhio)methyl]thio]phenylacetyl]amino]-8-oxo-5-thia-1-azabicyclo[4.2.0]oct-2-ene-2-carboxylic acid crystallizes, m.p. 174°175° (dec.). The salt is suspended in a little water while cooling with ice, layered over with ethyl acetate and acidified. From the ethyl acetate extract are isolated 1.2 gms. of pure DL-3-[(acetyloxy)methyl]-7β-[[[[(methylthio)methyl]thio]phenylacetyl]amino]-8-oxo-5-thia-1-azabicyclo[4.2.0]oct-2-ene-2-carboxylic acid.

EXAMPLE 9

DL-3-[(Acetyloxy)methyl]-7β-[[[[(methylthio)methyl]thio]phenylacetyl]amino]-8-oxo-5-thia-1-azabicyclo[4.2.0]oct-2-ene-2-carboxylic acid, sodium salt The product of Example 8 is neutralized with an equimolar amount of aqueous sodium bicarbonate solution. The solution is filtered and freeze dried to obtain DL-3-[(acetyloxy)methyl]-7β-[[[[(methylthio)methyl]thio]phenylacetyl]amino]-8-oxo-5-thia-1-azabicyclo[4.2.0]oct-2-ene-2-carboxylic acid, sodium salt, m.p. 185°–186° (dec.).

EXAMPLE 10

[[(Phenylthio)methyl]thio]acetic acid, methyl ester 14.8 gms. of potassium thiophenolate are combined with 15.4 gms. of (chloromethyl)thioacetic acid, methyl ester in 100 ml. of dimethylformamide while warming. This is stirred overnight at room temperature and then concentrated in a rotary evaporator. Water and ether are added to the residue. The ether phase is dried with magnesium sulfate, concentrated and distilled to obtain 16 gms. of [[(phenylthio)methyl]thio]acetic acid, methyl ester, b.p.$_{0.01}$ 123°–130°.

EXAMPLE 11

[[(Phenylthio)methyl]thio]acetic acid, potassium salt 50 ml. of 2 N potassium hydroxide in isopropanol are added to a solution of 20.8 gms. of [[(phenylthio)methyl]thio]acetic acid, methyl ester in 150 ml. of isopropanol. 20 gms. of [[(phenylthio)methyl]thio]acetic acid, potassium salt crystallize, m.p. 280°–283° (dec.).

Example 12

[[(Phenylthio)methyl]thio]acetyl chloride 5.1 gms. of [[(phenylthio)methyl]thio]acetic acid, potassium salt are treated with 5 gms. of oxalyl chloride in 10 ml. of methylene chloride at 0°–5° to obtain 3.4 gms. of [[(phenylthio)methyl]thio]acetyl chloride which is used further without purification.

EXAMPLE 13

DL-3-[(Actyloxy)methyl]-7-[[[[(phenylthio)methyl]thio]acetyl]amino-8-oxo-5-thia-1-azabicyclo[4.2.0]oct-2-ene-2-carboxylic acid 3.1 gms. of 7-aminocephalosporanic acid and 3.4 gms. of [[(phenylthio)methyl]thio]acetyl chloride are treated according to the procedure of Example 3 to obtain DL-3-[(acetyloxy)methyl]-7-[[[[(phenylthio)methyl]thio]acetyl]amino]-8-oxo-5-thia-1-azabicyclo[4.2.0]oct-2-ene-2-carboxylic acid. For purification, this product is converted to its potassium salt with potassium ethyl hexanoate. The reaction mixture is acidified and extracted with ethyl acetate to obtain the purified free acid. This is dissolved in methylene chloride and petroleum ether is added to the solution. The product precipitates in amorphous solid form.

EXAMPLE 14

[[[(Phenylmethyl)thio]methyl]thio]acetic acid, methyl ester

A mixture of 12.4 gms. of benzyl mercaptan, 15.4 gms. of chloromethyl)thioacetic acid, methyl ester and 14.0 ml. of triethylamine in 100 ml. of tetrahydrofuran are permitted to stand overnight. The mixture is filtered, concentrated and distilled to obtain [[[(phenylmethyl)thio]methyl]thio]acetic acid, methyl ester, b.p.$_{0.01-0.05}$ 150°–160°.

EXAMPLE 15

[[[(Phenylmethyl)thio]methyl]thio]acetic acid, potassium salt 26.0 ml. of 2 N methanolic potassium hydroxide are added to 10 gms. of the product of Example 14 in 50 ml. of isopropanol to obtain 7.8 gms. of [[[(phenylmethyl)thio]methyl]thio]acetic acid, potassium salt, m. p. >230°.

EXAMPLE 16

[[[(phenylmethyl)thio]methyl]thio]acetyl chloride 6.9 gms. of the product of Example 15 in 25 ml. of methylene chloride are treated at room temperature with 6.5 gms. of oxalyl chloride in 9 ml. of methylene chloride according to the procedure of Example 2. 5.9 gms. of the product, [[[(phenylmethyl)thio]methyl]thio]acetyl chloride, are obtained as an oil which is used further without purification.

EXAMPLE 17

DL-3-[(Acetyloxy)methyl]-7β-[[[[(phenylmethyl)thio]methyl]thio]acetylamino]-8-oxo-5-thia-1-azabicyclo[4.2.0]oct-2-ene-2-carboxylic acid 2.7 gms. of 7-aminocephalosporanic acid with an equimolar amount of triethylamine are dissolved in a mixture of 30 ml. of water and 30 ml. of acetone. A solution of 2.9 gms. of [[[(phenylmethyl)thio]methyl]thio]acetyl chloride is added dropwise at 0° to 5° with stirring and the pH is held at 7–7.5 by the simultaneous addition of triethylamine. The mixture is stirred for two hours at 0°–5° and then worked up by the procedure of Example 3. The yield of product, DL-3-[(acetyloxy)methyl]-7β-[[[[(phenylmethyl)thio]methyl]thio]acetylamino]-8-oxo-5-thia-1-azabicyclo[4.2.0]oct-2-ene-2-carboxylic acid, is 2,4 gms. This product is purified by dissolving in 10 ml. of methanol and neutralizing by means of a 10% solution of dicyclohexylamine in isopropanol. 2.3 gms. of the dicyclohexylamine salt crystallize, m.p. 168°–170° (dec.). To obtain the free acid, the salt is suspended in 100 ml. of ethyl acetate, 100 ml. of water are added and this is acidified with 2 N hydrochloric acid. On concentrating the ethyl acetate phase, an oily residue is obtained which solidifies upon trituration with petroleum ether. The product, DL-3-[(acetyloxy)methyl]-7β-[[[[(phenylmethyl)thio]methyl]thio]acetylamino]-8-oxo-5-thia-1-azabicyclo[4.2.0]oct-2-ene-2-carboxylic acid, melts at 75°–78° (dec.).

EXAMPLE 18

DL-3-[(Acetyloxy)methyl]-7β-[[[[(phenylmethyl)thio]methyl]thio]acetylamino]-8-oxo-5-thia-1-azabicyclo[4.2.0]oct-2-ene-2-carboxylic acid, sodium salt 1.1 gm. of the acid obtained in Example 17 are dissolved in 20 ml. of methanol and the solution is neutralized with 22 ml. of 0.1 N sodium bicarbonate solution. This is filtered and the methanol is evaporated in a rotary evaporator. The residual aqueous solution is freeze dried to obtain 1.1 gm. of DL-3-[(acetyloxy)methyl]-7β-[[[[(phenylmethyl)thio]methyl]thio]acetylamino]-8-oxo-5-thia-1-azabicyclo[4.2.0]oct-2-ene-2-carboxylic acid, sodium salt, m.p. 110°–112° (dec.).

The following additional products having the formula (c) in the table are obtained by the procedure of Examples 7, 8 and 9 by substituting for the 7-aminocephalosporanic acid, the starting material (a), and for the DL-β-[[(methylthio)thio]benzeneacetic acid, the starting material (b) with the substituents indicated in the table:

TABLE

| Example | (a) R | (b) $R_1$ | $R_2$ | $R_3$ | (c) $R_4$ |
|---|---|---|---|---|---|
| 19 | —CH$_3$ | H | —C$_3$H$_7$ | —C$_3$H$_7$ | H |
| 20 | —C$_2$H$_5$ | —CH$_3$ | —C$_2$H$_5$ | —CH$_3$ | —OH |
| 21 | —CH$_2$C$_6$H$_5$ | —C$_3$H$_7$ | H | —C$_2$H$_5$ | —OCOCH$_3$ |
| 22 | —CH$_2$OC(O)—CH(CH$_3$)$_2$ | —C$_6$H$_5$ | H | —CH$_2$C$_6$H$_5$ | —OCOCH$_3$ |
| 23 | —CH$_2$OC(O)—C$_6$H$_5$ | —C$_6$H$_5$ | —CH$_3$ | —CH$_3$ | —OCOCH$_3$ |
| 24 | —C$_2$H$_4$—C$_6$H$_5$ | —C$_6$H$_5$ | —C$_2$H$_5$ | —CH$_3$ | H |
| 25 | —CH(C$_6$H$_5$)$_2$ |  | —C$_2$H$_5$ | —CH$_3$ | —OCOCH$_3$ |

TABLE-continued

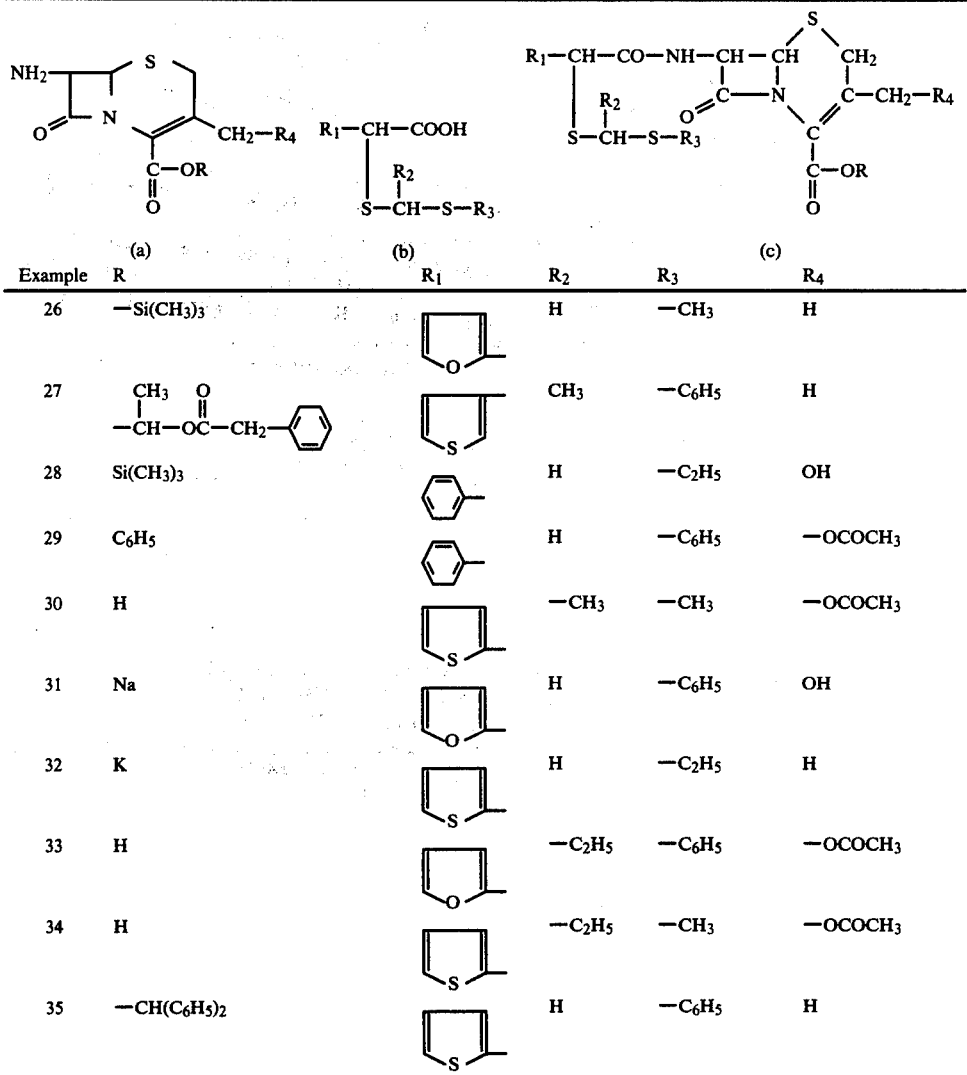

| Example | (a) R | (b) R₁ | R₂ | R₃ | (c) R₄ |
|---|---|---|---|---|---|
| 26 | —Si(CH₃)₃ | furyl | H | —CH₃ | H |
| 27 | -CH(CH₃)-O-CO-CH₂-C₆H₅ | thienyl | CH₃ | —C₆H₅ | H |
| 28 | Si(CH₃)₃ | phenyl | H | —C₂H₅ | OH |
| 29 | C₆H₅ | phenyl | H | —C₆H₅ | —OCOCH₃ |
| 30 | H | thienyl | —CH₃ | —CH₃ | —OCOCH₃ |
| 31 | Na | furyl | H | —C₆H₅ | OH |
| 32 | K | thienyl | H | —C₂H₅ | H |
| 33 | H | furyl | —C₂H₅ | —C₆H₅ | —OCOCH₃ |
| 34 | H | thienyl | —C₂H₅ | —CH₃ | —OCOCH₃ |
| 35 | —CH(C₆H₅)₂ | thienyl | H | —C₆H₅ | H |

What is claimed is:

1. A compound of the formula

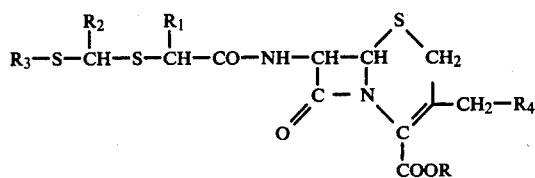

wherein R is hydrogen, lower alkyl, phenyl-lower alkyl, diphenylmethyl, tri(lower alkyl)silyl,

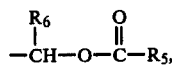

alkali metal, alkaline earth metal, or dicyclohexylamine, triethylamine or (lower alkyl)amine salt; $R_1$ is hydrogen, lower alkyl, phenyl, thienyl or furyl; $R_2$ and $R_6$ each is hydrogen or lower alkyl; $R_3$ and $R_5$ each is lower alkyl, phenyl or phenyl-lower alkyl; and $R_4$ is hydrogen, hydroxy or lower alkanoyloxy; said lower alkyl and lower alkanoyloxy groups having up to seven carbon atoms.

2. A compound as in claim 1 wherein R is hydrogen, alkali metal, diphenylmethyl or

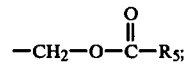

$R_1$ is hydrogen or phenyl, $R_2$ is hydrogen; $R_3$ is lower alkyl, phenyl or phenyl-lower alkyl; $R_4$ is hydrogen or acetoxy; and $R_5$ is methyl or t-butyl.

3. A compound as in claim 1 wherein R, $R_1$ and $R_2$ each is hydrogen, $R_3$ is lower alkyl and $R_4$ is lower alkanoyloxy.

4. A compound as in claim 3 wherein the lower alkyl group is methyl and the lower alkanoyloxy group is acetoxy.

5. A compound as in claim 1 wherein R is alkali metal, $R_1$ and $R_2$ each is hydrogen, $R_3$ is methyl and $R_4$ is acetoxy.

6. A compound as in claim 1 wherein R and $R_2$ each is hydrogen; $R_1$ is phenyl; $R_3$ is lower alkyl and $R_4$ is lower alkanoyloxy.

7. A compound as in claim 6 wherein the lower alkyl group is methyl and the lower alkanoyloxy group is acetoxy.

8. A compound as in claim 1 wherein R, R₁ and R₂ each is hydrogen, R₃ is phenyl and R₄ is lower alkanoyloxy.

9. A compound as in claim 8 wherein the lower alkanoyloxy group is acetoxy.

10. A compound as in claim 1 wherein R, R₁ and R₂ each is hydrogen, R₃ is phenyl-lower alkyl and R₄ is acetoxy.

11. A compound as in claim 10 wherein the phenyl-lower alkyl group is benzyl.

12. A compound as in claim 1 wherein R is alkali metal, R₁ and R₂ each is hydrogen, R₃ is benzyl and R₄ is acetoxy.

13. The compound of the formula

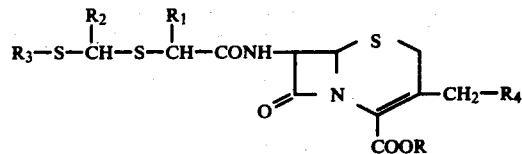

wherein R is —CH₃, R₁ is H, R₂ is —C₃H₇, R₃ is —C₃H₇ and R₄ is H.

14. A compound as in claim 1 wherein R is hydrogen, lower alkyl or alkali metal, R₁ and R₂ each is hydrogen, R₃ is lower alkyl and R₄ is hydrogen or lower alkanoyloxy.

15. A compound of the formula

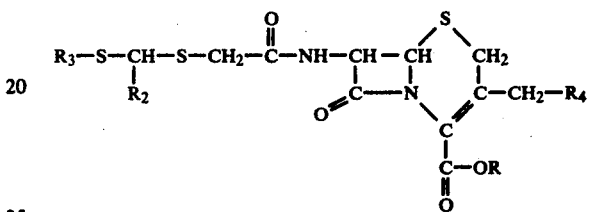

wherein
R is hydrogen, lower alkyl or alkali metal;
R₂ is hydrogen or lower alkyl;
R₃ is lower alkyl; and
R₄ is hydrogen or lower alkanoyloxy.

* * * * *

UNITED STATES PATENT AND TRADEMARK OFFICE
CERTIFICATE OF CORRECTION

PATENT NO. : 4,171,435
DATED : October 16, 1979
INVENTOR(S) : Hermann Breuer, Uwe D. Treuner It is certified that error appears in the above-identified patent and that said Letters Patent are hereby corrected as shown below:

Col. 1, line 40, "hydroen" should read -- hydrogen --.
Col. 4, line 9 "thioactic" should read -- thioacetic --.
Col. 5, line 11 "60-" should read -- 6α --.
Col. 5, line 46 "mthyl" should read -- methyl --.
Col. 5, line 51 "Example" should read -- Example 8 --.
Col. 5, line 62 "(methylhio)" should read -- (methylthio) --.
Col. 6, line 52 "(Actyloxy)" should read -- (Acetyloxy) --.
Col. 8, line 39 "DL-β-" should read -- DL-α- --.

Signed and Sealed this

Fifth Day of August 1980

[SEAL]

Attest:

SIDNEY A. DIAMOND

Attesting Officer

Commissioner of Patents and Trademarks